(12) United States Patent
Tatsumi et al.

(10) Patent No.: US 10,150,983 B2
(45) Date of Patent: Dec. 11, 2018

(54) METHOD FOR MEASURING INDOXYL SULFURIC ACID

(71) Applicant: Nipro Corporation, Osaka (JP)

(72) Inventors: Kenta Tatsumi, Kyoto (JP); Daisuke Nakamura, Kyoto (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 14/768,331

(22) PCT Filed: Feb. 18, 2014

(86) PCT No.: PCT/JP2014/053777
§ 371 (c)(1),
(2) Date: Sep. 29, 2015

(87) PCT Pub. No.: WO2014/129460
PCT Pub. Date: Aug. 28, 2014

(65) Prior Publication Data
US 2016/0032354 A1 Feb. 4, 2016

(30) Foreign Application Priority Data
Feb. 19, 2013 (JP) ................. 2013-029698

(51) Int. Cl.
*C12Q 1/44* (2006.01)
*C12N 9/16* (2006.01)

(52) U.S. Cl.
CPC ............. *C12Q 1/44* (2013.01); *C12N 9/16* (2013.01); *C07K 2319/21* (2013.01); *G01N 2333/916* (2013.01); *G01N 2800/347* (2013.01)

(58) Field of Classification Search
CPC ...................................... C12N 9/16
See application file for complete search history.

(56) References Cited

U.S. PATENT DOCUMENTS

| 5,919,644 A | 7/1999 | Adachi et al. |
| 5,958,675 A | 9/1999 | Wicks et al. |

FOREIGN PATENT DOCUMENTS

| JP | 9-168397 | 6/1997 |
| JP | 2002-513288 A | 5/2002 |
| JP | 2007-020434 A | 2/2007 |
| JP | 4183777 B2 | 11/2008 |
| JP | 2012-082181 | 4/2012 |
| JP | 2012-237623 | 12/2012 |
| JP | 2013-032316 | 2/2013 |

OTHER PUBLICATIONS

Beil et al., Purification and characterization of the arylsulfatase synthesized by pseudomonas aeruginosa PAO during growth in sulfate-free medium and cloning of the arylsulfatase gene (atsa), Eur. J. Biochem., 229:385-94 (1995).
Wang et al., Purple urine bag syndrome in a hemodialysis patient, Intern. Med., 44(8):859-61 (2005).
Niwa et al., Indoxyl sulfate in hemodialysis patients, Nihon Toseki Igakkai Zasshi, 21(10):951-6 (1988).
International Application No. PCT/JP2014/053777, International Search Report and Written Opinion (English translation), dated Apr. 8, 2014.
International Application No. PCT/JP2014/053777, International Preliminary Report on Patentability, dated Aug. 25, 2015.
Japanese patent application No. 2015-501459, English translation of Notification of Reason for Refusal, dated Oct. 10, 2017.

*Primary Examiner* — Bin Shen
(74) *Attorney, Agent, or Firm* — Marshall, Gerstein & Borun LLP

(57) ABSTRACT

It is an object of this invention to provide a simple measurement method capable of detecting indoxyl sulfuric acid in a sample rapidly and at high sensitivity. By causing sulfatase and tetrazolium salt to act on indoxyl sulfuric acid in a sample to generate a formazan dye, and then calculating the generation amount of the formazan dye, indoxyl sulfuric acid in the sample can be measured more simply, more rapidly, and at higher sensitivity as compared with former methods.

17 Claims, 3 Drawing Sheets

Specification includes a Sequence Listing.

SEQUENCE LISTING

```
<160> NUMBER OF SEQ ID NOS: 6

<210> SEQ ID NO 1
<211> LENGTH: 536
<212> TYPE: PRT
<213> ORGANISM: Pseudomonas aeruginosa

<400> SEQUENCE: 1

Met Ser Lys Arg Pro Asn Phe Leu Val Ile Val Ala Asp Asp Leu Gly
1               5                   10                  15

Phe Ser Asp Ile Gly Ala Phe Gly Gly Glu Ile Ala Thr Pro Asn Leu
            20                  25                  30

Asp Ala Leu Ala Ile Ala Gly Leu Arg Leu Thr Asp Phe His Thr Ala
        35                  40                  45

Ser Thr Cys Ser Pro Thr Arg Ser Met Leu Leu Thr Gly Thr Asp His
    50                  55                  60
```

-continued

```
His Ile Ala Gly Ile Gly Thr Met Ala Glu Ala Leu Thr Pro Glu Leu
 65                  70                  75                  80

Glu Gly Lys Pro Gly Tyr Glu Gly His Leu Asn Glu Arg Val Val Ala
                 85                  90                  95

Leu Pro Glu Leu Leu Arg Glu Ala Gly Tyr Gln Thr Leu Met Ala Gly
            100                 105                 110

Lys Trp His Leu Gly Leu Lys Pro Glu Gln Thr Pro His Ala Arg Gly
            115                 120                 125

Phe Glu Arg Ser Phe Ser Leu Leu Pro Gly Ala Ala Asn His Tyr Gly
            130                 135                 140

Phe Glu Pro Pro Tyr Asp Glu Ser Thr Pro Arg Ile Leu Lys Gly Thr
145                 150                 155                 160

Pro Ala Leu Tyr Val Glu Asp Glu Arg Tyr Leu Asp Thr Leu Pro Glu
                165                 170                 175

Gly Phe Tyr Ser Ser Asp Ala Phe Gly Asp Lys Leu Leu Gln Tyr Leu
                180                 185                 190

Lys Glu Arg Asp Gln Ser Arg Pro Phe Phe Ala Tyr Leu Pro Phe Ser
            195                 200                 205

Ala Pro His Trp Pro Leu Gln Ala Pro Arg Glu Ile Val Glu Lys Tyr
            210                 215                 220

Arg Gly Arg Tyr Asp Ala Gly Pro Glu Ala Leu Arg Gln Glu Arg Leu
225                 230                 235                 240

Ala Arg Leu Lys Glu Leu Gly Leu Val Glu Ala Asp Val Glu Ala His
                245                 250                 255

Pro Val Leu Ala Leu Thr Arg Glu Trp Glu Ala Leu Glu Asp Glu Glu
                260                 265                 270

Arg Ala Lys Ser Ala Arg Ala Met Glu Val Tyr Ala Ala Met Val Glu
            275                 280                 285

Arg Met Asp Trp Asn Ile Gly Arg Val Val Asp Tyr Leu Arg Arg Gln
            290                 295                 300

Gly Glu Leu Asp Asn Thr Phe Val Leu Phe Met Ser Asp Asn Gly Ala
305                 310                 315                 320

Glu Gly Ala Leu Leu Glu Ala Phe Pro Lys Phe Gly Pro Asp Leu Leu
                325                 330                 335

Gly Phe Leu Asp Arg His Tyr Asp Asn Ser Leu Glu Asn Ile Gly Arg
            340                 345                 350

Ala Asn Ser Tyr Val Trp Tyr Gly Pro Arg Trp Ala Gln Ala Ala Thr
            355                 360                 365

Ala Pro Ser Arg Leu Tyr Lys Ala Phe Thr Thr Gln Gly Gly Ile Arg
            370                 375                 380

Val Pro Ala Leu Val Arg Tyr Pro Arg Leu Ser Arg Gln Gly Ala Ile
385                 390                 395                 400

Ser His Ala Phe Ala Thr Val Met Asp Val Thr Pro Thr Leu Leu Asp
                405                 410                 415

Leu Ala Gly Val Arg His Pro Gly Lys Arg Trp Arg Gly Arg Glu Ile
            420                 425                 430

Ala Glu Pro Arg Gly Arg Ser Trp Leu Gly Trp Leu Ser Gly Glu Thr
            435                 440                 445

Glu Ala Ala His Asp Glu Asn Thr Val Thr Gly Trp Glu Leu Phe Gly
            450                 455                 460

Met Arg Ala Ile Arg Gln Gly Asp Trp Lys Ala Val Tyr Leu Pro Ala
465                 470                 475                 480

Pro Val Gly Pro Ala Thr Trp Gln Leu Tyr Asp Leu Ala Arg Asp Pro
```

```
                485             490             495
Gly Glu Ile His Asp Leu Ala Asp Ser Gln Pro Gly Lys Leu Ala Glu
                500             505             510

Leu Ile Glu His Trp Lys Arg Tyr Val Ser Glu Thr Gly Val Val Glu
                515             520             525

Gly Ala Ser Pro Phe Leu Val Arg
                530             535
```

<210> SEQ ID NO 2
<211> LENGTH: 1611
<212> TYPE: DNA
<213> ORGANISM: Pseudomonas aeruginosa

<400> SEQUENCE: 2

```
atgagcaaac gccccaactt cctggtgatc gtcgccgacg acctgggctt ctccgatatc    60
ggcgccttcg gcggcgagat cgccacgccg aacctcgacg ccctggccat cgccggcctg   120
cgcctgaccg acttccacac cgcctcgacc tgctcgccga cccgctcgat gctgctcacc   180
ggcaccgacc accacatcgc cgggatcggc accatggccg aggcgctgac cccggaactg   240
gaaggcaagc gggttacga agggcatctc aacgagcgcg tggtggcgct gccggagctg   300
ctccgcgagg ccggctacca gaccctcatg gccggcaagt ggcacctcgg tctgaagccg   360
gaacagacgc cccatgcacg cggttttcgag cgttccttct cgctgctgcc gggcgccgcc   420
aaccactatg gtttcgagcc gccctacgac gaaagcactc gcgcatcct caagggtacg    480
ccagcgctct acgtggaaga cgagcgctac ctcgacacgc tgccggaggg cttctattcc   540
tccgacgcct tcggcgacaa gctgctgcaa tacctcaagg agcgcgacca gagccggccg   600
ttcttcgcct acctgccgtt ctccgcgccg cactggccgc tgcaagcgcc gcgggagatc   660
gtcgagaagt accgcggtcg ctacgacgcc ggtccagaag cgctgcgcca ggaacgcctg   720
gcccggctca aggagctggg cctggtggaa gcggacgtcg aagcccatcc ggtgctcgcc   780
ctgacccgcg agtgggaggc cctggaggac gaggaacggg ctaagtcggc gcgggcgatg   840
gaggtctacg cggcgatggt cgagcgcatg actggaaaca tcggcagggt cgtggactac   900
ctgcgccggc agggcgagct ggacaacacc ttcgtcctgt tcatgtccga caacggcgcc   960
gaaggcgccc tgctggaggc gttcccgaaa ttcggcccgg acctgctggg ctttctcgac  1020
cggcactacg acaacagcct ggaaaacatc ggccgcgcca ttcctacgt ctggtatggc   1080
ccgcgctggg cccaggcggc caccgcacca tcgcgcctgt acaaggcgtt caccacccag  1140
ggcgggattc gcgtgccagc gctggtgcgc tacccgcggc taagccggca gggtgcgatc  1200
agccatgcct tcgccacggt gatggacgtc accccgaccc tcctcgacct cgccggtgtc  1260
cgccacccag gcaagcgctg gcgcggccgc gagatcgccg agccgcgcgg caggtcgtgg  1320
ctgggttggc tttccggcga gaccgaggcg gcccacgacg agaacaccgt gaccggctgg  1380
gagctgttcg gcatgcgtgc gatccgccag ggcgactgga aggcggtgta cctgccggcc  1440
ccggtgggcc cggccaccct gcagctctac gacctggccc gcgacccggg cgagatccac  1500
gacctcgctg acagccagcc gggcaagctg gcggagctga tcgagcattg gaagcgatac  1560
gtcagcgaga ccggtgtcgt agagggggct tcgcctttcc tggtgcgata a           1611
```

<210> SEQ ID NO 3
<211> LENGTH: 32
<212> TYPE: DNA
<213> ORGANISM: artificial sequence
<220> FEATURE:

```
<223> OTHER INFORMATION: nucleotide sequence of forwad primer used for
      amplifying sulfatase gene.

<400> SEQUENCE: 3
ggaattcatg agcaaacgcc ccaacttcct gg                                    32

<210> SEQ ID NO 4
<211> LENGTH: 34
<212> TYPE: DNA
<213> ORGANISM: artificial sequence
<220> FEATURE:
<223> OTHER INFORMATION: nucleotide sequence of reverse primer used for
      amplifying sulfatase gene.

<400> SEQUENCE: 4
cgcgtcgact tatcgcacca ggaaaggcga agcc                                  34

<210> SEQ ID NO 5
<211> LENGTH: 30
<212> TYPE: DNA
<213> ORGANISM: artificial sequence
<220> FEATURE:
<223> OTHER INFORMATION: nucldotide sequence of forwad primer used for
      inverse PCR.

<400> SEQUENCE: 5
ggtctgtttc ctgtgtgaaa ttgttatccg                                       30

<210> SEQ ID NO 6
<211> LENGTH: 23
<212> TYPE: DNA
<213> ORGANISM: artificial sequence
<220> FEATURE:
<223> OTHER INFORMATION: nucleotide sequence of reverse primer used for
      inverse PCR.

<400> SEQUENCE: 6
atgagcaaac gccccaactt cct                                              23
```

METHOD FOR MEASURING INDOXYL SULFURIC ACID

TECHNICAL FIELD

The present invention relates to a technique capable of detecting indoxyl sulfuric acid in a sample simply and at high sensitivity.

BACKGROUND ART

Indoxyl sulfuric acid is a tryptophan metabolite derived from food protein and is known as a uremia substance. The uremia substance is stored in the body with progress of renal dysfunction and causes uremia symptoms, such as loss of appetite, nausea, and vomiting. In actual, it has been reported that the concentration of indoxyl sulfuric acid in serum markedly increases in chronic renal failure patients and is about 60 times that of normal persons (e.g., Non patent literature 1). Therefore, it is very useful for diagnosis and examination of diseases to measure the indoxyl sulfuric acid concentration in serum. Further, the measurement method can be utilized for the judgment of therapeutic effects, prognostic prediction, selection of prescription foods of dietary therapy, and the like.

Heretofore, the measurement of indoxyl sulfuric acid has been performed mainly using gas chromatography and high performance liquid chromatography. These methods have been excellent in sensitivity or accuracy but have had problems in that skill has been required for analysis, high cost has been required for measuring devices or facilities, and the like. On the other hand, an EIA method (enzyme immunoassay) using an antibody specific to indoxyl sulfuric acid has been reported as a method for measuring indoxyl sulfuric acid without using the devices (e.g., Patent Literature 1). However, the measurement method utilizing an antigen-antibody reaction has had problems in that the measuring time is long and an operation for the measurement is complicated.

Under the circumstances, a development of a method capable of simply measuring indoxyl sulfuric acid concentration rapidly and correctly without using an expensive measuring device has been demanded.

CITATION LIST

Patent Literature 1: Japanese Patent No. 4183777 Non Patent Literature 1: Japanese Soc. for Dialysis Therapy Journal, 21 (10) 951-956 (1988)

DISCLOSURE OF INVENTION

Problems to be Solved by the Invention

It is an object of the present invention to provide a simple measurement method capable of detecting indoxyl sulfuric acid in a sample rapidly and at high sensitivity. Furthermore, it is another object of the present invention to provide a kit for measuring indoxyl sulfuric acid and a method for examining renal function utilizing the measurement method.

Means for Solving the Problems

The present inventors have extensively conducted examination in order to solve the above-described problems. As a result, the present inventors have found that, by causing sulfatase and tetrazolium salt to act on indoxyl sulfuric acid in a sample to generate a formazan dye, and then calculating the generation amount of the formazan dye, the indoxyl sulfuric acid in the sample can be measured more simply, more rapidly, and at higher sensitivity as compared with former methods. Moreover, the present inventors also have found that sulfatase derived from *Pseudomonas* among various kinds of sulfatase has high activity to hydrolyze a sulfuric acid part of indoxyl sulfuric acid, and then, by using the sulfatase derived from *Pseudomonas*, indoxyl sulfuric acid can be measured more rapidly and at higher sensitivity. Furthermore, the present inventors also have found that, by allowing albumin to coexist when causing sulfatase and tetrazolium salt to act on the indoxyl sulfuric acid in the sample, the dilution linearity of the sample is improved. Moreover, the present inventors also have found that, by allowing an anionic surfactant and/or a thiol compound to coexist when causing sulfatase and tetrazolium salt to act on the indoxyl sulfuric acid in the sample, the dilution linearity of the sample is improved and also the sensitivity is further improved. The present invention has been completed as a result of further repeatedly conducting a research based on these findings.

More specifically, the present invention provides a method for measuring indoxyl sulfuric acid, a kit for measuring indoxyl sulfuric acid, and a method for detecting renal function of the following aspects.

Item 1. A method for measuring indoxyl sulfuric acid contained in a sample, having a process of causing sulfatase and tetrazolium salt to act on the sample, and then measuring a generated formazan dye.

Item 2. The measurement method according to Item 1, in which the sulfatase is aryl sulfatase.

Item 3. The measurement method according to Item 1 or 2, in which the sulfatase is derived from at least one kind of microorganism selected from the group consisting of *Pseudomonas, Mycobacterium, Acinetobacter, Streptomyces*, and *Aspergillus*.

Item 4. The measurement method according to any one of Items 1 to 3, in which the sulfatase is derived from bacteria belonging to *Pseudomonas*.

Item 5. The measurement method according to any one of Items 1 to 4, in which the sulfatase is derived from *Pseudomonas aeruginosa*.

Item 6. The measurement method according to any one of Items 1 to 5, in which the sulfatase is aryl sulfatase containing polypeptide of any one of the following items (i) to (iv):

(i) Polypeptide containing an amino acid sequence represented by SEQ ID NO: 1;

(ii) Polypeptide containing an amino acid sequence in which one or more amino acid residues are substituted, deleted, added, or inserted in the amino acid sequence represented by SEQ ID NO: 1 and having an activity to catalyze a hydrolysis reaction of indoxyl sulfuric acid equal to or higher than the activity of the polypeptide (i) above;

(iii) Polypeptide containing an amino acid sequence having 60% or more sequence identity to the amino acid sequence represented by SEQ ID NO: 1 and having an activity to catalyze a hydrolysis reaction of indoxyl sulfuric acid equal to or higher than the activity of the polypeptide (i) above; and (iv) Polypeptide containing an amino acid sequence coded by a base sequence which can be hybridized to a complementary sequence of a base sequence represented by SEQ ID NO: 2 under stringent conditions and having an activity to catalyze a hydrolysis reaction of indoxyl sulfuric acid equal to or higher than the activity of the polypeptide (i) above.

Item 7. The measurement method according to any one of Items 1 to 6, in which the sulfatase and the tetrazolium salt are caused to act on the sample in the presence of albumin.

Item 8. The measurement method according to any one of Items 1 to 7, in which the sulfatase and the tetrazolium salt are caused to act on the sample in the presence of at least one selected from the group consisting of an anionic surfactant and a thiol compound.

Item 9. A kit for measuring indoxyl sulfuric acid, containing sulfatase and tetrazolium salt.

Item 10. The measurement kit according to Item 9, containing a first reagent containing tetrazolium salt and a second reagent containing sulfatase.

Item 11. The measurement kit according to Item 9 or 10, further containing albumin.

Item 12. The measurement kit according to any one of Items 9 to 11, further containing at least one selected from the group consisting of an anionic surfactant and a thiol compound.

Item 13. The measurement kit according to any one of Items 9 to 12, which is used for diagnosis of renal function.

Item 14. The measurement kit according to any one of Items 9 to 13, which is used for diagnosis of renal failure.

Item 15. A method for examining renal function, including a process of causing sulfatase and tetrazolium salt to act on a sample extracted from a living body, and then measuring a generated formazan dye.

Item 16. The examination method according to Item 15, in which the sample is blood, serum, plasma, or urine.

Item 17. The examination method according to Item 15 or 16, which is used for examination of renal failure.

Advantages

According to the measurement method of the present invention, indoxyl sulfuric acid in a sample can be measured rapidly and at high sensitivity by a simple technique. Therefore, by utilizing the measurement method of the present invention, a renal dysfunction which becomes clear from the amount of indoxyl sulfuric acid can be easily detected and judgment of renal function, examination and diagnosis of diseases accompanied by a renal disease functional disorder, and the like can be simply performed.

EMBODIMENTS FOR CARRYING OUT THE INVENTION

1. Method for Measuring Indoxyl Sulfuric Acid

A measurement method of the present invention is a method for measuring indoxyl sulfuric acid contained in a sample and has a process of causing sulfatase and tetrazolium salt to act on a sample, and then measuring a generated formazan dye. Hereinafter, the measurement method of the present invention is described in detail.

Mechanism of Indoxyl Sulfuric Acid Measurement

Figure 1:
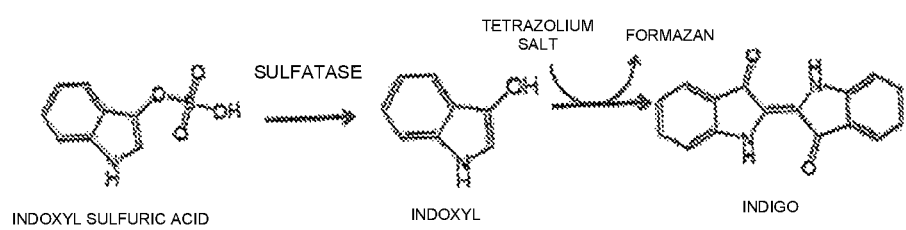
FIG. 1 is a view showing the reaction mechanism in a method for measuring indoxyl sulfuric acid of the present invention.

Although a restrictive interpretation of the present invention is not desired, it is considered that the measurement of the present invention enables measurement of indoxyl sulfuric acid by the mechanism shown in FIG. 1. More specifically, indoxyl sulfuric acid in a sample is hydrolyzed by causing sulfatase to act thereon, so that indoxyl is generated. The generated indoxyl is easily oxidized to be indigo. However, when tetrazolium salt coexists in that case, tetrazolium salt is reduced, so that a formazan dye is generated. The formazan dye reflects the indoxyl sulfuric acid concentration in the sample. Therefore, the indoxyl sulfuric acid in the sample can be quantified by colorimetrically determining the generated formazan dye.

Sample

In the measurement method of the present invention, the sample serving as the measuring target of indoxyl sulfuric acid is not particularly limited insofar as the presence or absence of indoxyl sulfuric acid and the measurement of the concentration thereof are needed, and a sample derived from a living body, an experiment sample, and the like are mentioned, for example. In particular, the correlation between the amount of indoxyl sulfuric acid in a living body and renal function is known, and therefore a sample derived from a living body extracted for examination of renal function is mentioned as a suitable example of the sample. Specific examples of such a sample derived from a living body include blood, serum, plasma, urine, and the like. Among the above, from the viewpoint that the state of renal function is more correctly reflected, blood, serum, and plasma are preferably mentioned and serum and plasma are more preferably mentioned. The origin of the sample derived from a living body is not particularly limited and mammals are mentioned, for example, and human beings are preferable.

The sample may be subjected to pretreatment, such as removal of impurities, as necessary, when subjected to the measurement method of the present invention.

Sulfatase

The sulfatase to be used in the present invention is not particularly limited insofar as the sulfatase has an activity to catalyze a reaction of hydrolyzing indoxyl sulfuric acid and isolate a sulfuric acid group, and aryl sulfatase (EC3.1.6.1) is preferably mentioned.

Moreover, the sulfatase to be used in the present invention preferably has both features that the Km value is small and the action pH is neutral to weakly alkaline from the viewpoint of increasing the measurement accuracy of indoxyl sulfuric acid. The indoxyl sulfuric acid concentration in the sample derived from a living body is very low, and thus high sensitivity is required. Therefore, the measurement accuracy can be increased as the Km value is smaller. Moreover, in the measurement method of the present invention, since the reaction pH of the tetrazolium salt is neutral to weakly alkaline, a formazan dye can be efficiently generated due to that fact that the action pH of the sulfatase is almost equal to the reaction pH of the tetrazolium salt.

The origin of the sulfatase to be used in the present invention is not particularly limited and microorganisms, mollusks, and the like are mentioned.

Examples of the microorganisms producing the sulfatase to be used in the present invention include, for example, bacteria belonging to *Pseudomonas, Mycobacterium, Acine-* tobacter, Streptomyces, Klebsiella, Enterobacter, Serratia, Citrobacter, Escherichia, Jiechia, Gurashikora, Sphingomonas, Wicker momyces, Pseudoalteromonas, Sphingobium, Methylibium, and the like; and fungi, such as Aspergillus, Candida, Arthroderma, Trichophyton, Penicillium, Uncinocarpus, Schizophyllum, Exophiala, Nectria, Magnaporthe, Talaromyces, Scheffersomyce, Macrophomina, Fusarium, Kluyveromyces, Lachancea, Zygosaccharomyces, Trichoderma, Lodderomyces, Meyerozyma, Botryotinia, Wallemia, Colletotrichum, Spathaspora, Cordyceps, Neosartorya, Debaryomyces, Verticillium, Yarrowia, and Ustilago.

Specific examples of the fungi belonging to Aspergillus include Aspergillus oryzae, Aspergillus niger, Aspergillus nidulans, Aspergillus fumigatus, Aspergillus terreus, Aspergillus flavus, Aspergillus clavatus, Aspergillus kawachii, and the like. Specific examples of the fungi belonging to Candida include Candida albicans, Candida tropicalis, Candida tenuis, Candida dubliniensis, Candida orthopsilosis, Candida parapsilosis, and the like. Specific examples of the fungi belonging to Arthroderma include Arthroderma benhamiae, Arthroderma gypseum, Arthroderma otae, and the like. Specific examples of the fungi belonging to Trichophyton include Trichophyton tonsurans, Trichophyton equinum, Trichophyton rubrum, Trichophyton verrucosum, and the like. Specific examples of the fungi belonging to Penicillium include Penicillium chrysogenum and the like. Specific examples of the fungi belonging to Uncinocarpus include Uncinocarpus reesii and the like. Specific examples of fungi belonging to Ogataea include Ogataea parapolymorpha and the like. Specific examples of the fungi belonging to Schizophyllum include Schizophyllum commune and the like. Specific examples of the fungi belonging to Exophiala include Exophiala dermatitidis and the like. Specific examples of the fungi belonging to Nectria include Nectria haematococca and the like. Specific examples of the fungi belonging to Magnaporthe include Magnaporthe oryzae and the like. Specific examples of the fungi belonging to Talaromyces include Talaromyces marneffei, Talaromyces stipitatus, and the like. Specific examples of the fungi belonging to Scheffersomyces include Scheffersomyces stipitis and the like. Specific examples of the fungi belonging to Macrophomina include Macrophomina phaseolina and the like. Specific examples of the fungi belonging to Fusarium include Fusarium pseudograminearum, Fusarium oxysporum, and the like. Specific examples of the fungi belonging to Kluyveromyces include Kluyveromyces lactis and the like. Specific examples of the fungi belonging to Lachancea include Lachancea thermotolerans and the like. Specific examples of the fungi belonging to Zygosaccharomyces include Zygosaccharomyces rouxii and the like. Specific examples of fungi belonging to Schizosaccharomyces include Schizosaccharomyces pombe and the like. Specific examples of the fungi belonging to Trichoderma include Trichoderma virens, Trichoderma atroviride, Trichoderma reesei, and the like. Specific examples of fungi belonging to Clavispora include Clavispora lusitaniae and the like. Specific examples of the fungi belonging to Lodderomyces include Lodderomyces elongisporus and the like. Specific examples of the fungi belonging to Meyerozyma include Meyerozyma guilliermondii, Millerozyma farinosa, and the like. Specific examples of fungi belonging to Beauveria include Beauveria bassiana and the like. Specific examples of the fungi belonging to Botryotinia include Botryotinia fuckeliana and the like. Specific examples of the fungi belonging to Wallemia include Wallemia sebi and the like. Specific examples of the fungi belonging to Colletotrichum include Colletotrichum gloeosporioides and the like. Specific examples of the fungi belonging to Spathaspora include Spathaspora passalidarum and the like. Specific examples of the fungi belonging to Cordyceps include Cordyceps militaris and the like. Specific examples of the fungi belonging to Neosartorya include Neosartorya fischeri and the like. Specific examples of the fungi belonging to Debaryomyces include Debaryomyces hansenii and the like. Specific examples of the fungi belonging to Verticillium include Verticillium albo-atrum and the like. Specific examples of the fungi belonging to Yarrowia include Yarrowia lipolytica and the like. Specific examples of the fungi belonging to Ustilago include Ustilago maydis and the like.

Examples of the mollusks producing the sulfatase to be used in the present invention include, for example, Helix pomatia, Abalone entrails, Patella vulgate, and the like.

From the viewpoint of measuring indoxyl sulfuric acid more rapidly and at higher sensitivity, as the origin of the sulfatase to be used in the present invention, those derived from microorganisms are preferably mentioned, those derived from Pseudomonas, Mycobacterium, Acinetobacter, Streptomyces, and Aspergillus are more preferably mentioned, those derived from Pseudomonas are still more preferably mentioned, and those derived from Pseudomonas aeruginosa are particularly preferably mentioned.

As a preferable example of the sulfatase to be used in the present invention, aryl sulfatase containing polypeptide of any one of the following items (i) to (iv) is mentioned:

(i) Polypeptide containing an amino acid sequence represented by SEQ ID NO: 1;

(ii) Polypeptide containing an amino acid sequence in which one or more amino acid residues are substituted, deleted, added, or inserted in the amino acid sequence represented by SEQ ID NO: 1 and having an activity to catalyze a hydrolysis reaction of indoxyl sulfuric acid equal to or higher than the activity of the polypeptide (i) above;

(iii) Polypeptide containing an amino acid sequence having 60% or more sequence identity to the amino acid sequence represented by SEQ ID NO: 1 and having an activity to catalyze a hydrolysis reaction of indoxyl sulfuric acid equal to or higher than the activity of the polypeptide (i) above; and (iv) Polypeptide containing an amino acid sequence coded by a base sequence which can be hybridized to a complementary sequence of a base sequence represented by SEQ ID NO: 2 under stringent conditions and having an activity to catalyze a hydrolysis reaction of indoxyl sulfuric acid equal to or higher than the activity of the polypeptide (i) above.

The polypeptide of (i) above is aryl sulfatase derived from Pseudomonas aeruginosa, is coded by a base sequence represented by SEQ ID NO: 2, and can be obtained as a gene product of a gene having the base sequence.

In the polypeptide of (ii) above, as the number of the amino acid residues to be substituted, deleted, added, or inserted is not particularly limited insofar as the polypeptide has an activity to catalyze a hydrolysis reaction of indoxyl sulfuric acid equal to or higher than the activity of the polypeptide of (i) above. The number of the amino acid residues is, for example, 1 to 20, preferably 1 to 15, more preferably 1 to 8, particularly preferably 1 to 5, and most preferably 1 to 3.

In the polypeptide of (ii) above, the substitution of the amino acid residue is preferably conservative substitution based on the properties of a side chain functional group and may be the non-conservative substitution, in which the properties of the amino acid residue before the substitution are different from the properties of the amino acid residue after the substitution, insofar as the polypeptide has an activity to catalyze a hydrolysis reaction of indoxyl sulfuric acid equal to or higher than the activity of the polypeptide of (i) above. Natural amino acids are classified into each category of nonpolar amino acids, non-charged amino acids, acidic amino acids, and basic amino acids according to a side chain functional group. The conservative substitution refers to substitution using an amino acid residue classified into the same category as the amino acid residue before the substitution. Herein, as the classification of amino acids, specifically, examples of the "nonpolar amino acids" include alanine, valine, leucine, isoleucine, proline, methionine, phenylalanine, and tryptophan; examples of the "non-charged amino acids" include glycine, serine, threonine, cysteine, tyrosine, asparagine, and glutamine; examples of the "acidic amino acids" include aspartic acid and glutamic acid; and the "basic amino acids" include lysine, arginine, and histidine.

In the polypeptide of (ii) above, the substitution, deletion, or addition of the amino acid residue is desirably introduced into a part other than a part participating in sulfatase activity in the polypeptide of (i) above. Examples of the part participating in the sulfatase activity in the polypeptide (i) above include aspartic acid at position 13, aspartic acid at position 14, cysteine at position 51, arginine at position 55, lysine at position 113, histidine at position 115, histidine at position 211, aspartic acid at position 317, aspartic acid at position 318, and lysine at position 375 in SEQ ID NO: 1. The part participating in the sulfatase activity in the polypeptide of (i) is disclosed in Structure, Vol. 9, 483-491, June, 2001 and the amino acid residue to be substituted, deleted, added, or inserted can be set as appropriate.

When introducing mutation, such as substitution, deletion, addition, and insertion, into the amino acid sequence, the mutation can be introduced according to known former methods. Examples of a method for introducing amino acid mutation include a site-specific mutation introducing method, for example. The method may be carried out by utilizing a technique based on Inverse PCR or a commercially available kit of QuikChange II Kit (manufactured by Stratagene). By the techniques mentioned above, polynucleotide (DNA) coding sulfatase having a desired mutation based on the base sequence represented by SEQ ID NO: 1 can be obtained. Then, sulfatase containing the polypeptide of (ii) above can be obtained as recombinant protein utilizing the obtained polynucleotide according to a known genetic engineering method described later.

In the polypeptide of (iii) above, the sequence identity to the amino acid sequence represented by SEQ ID NO: 1 is 60% or more and is not particularly limited insofar as the polypeptide has an activity to catalyze a hydrolysis reaction of indoxyl sulfuric acid equal to or higher than the activity of the polypeptide of (i) above. The sequence identity is preferably 65% or more, 70% or more, 75% or more, 80% or more, 85% or more, or 90% or more, more preferably 95% or more, and particularly preferably 96% or more, 97% or more, 98% or more, or 99% or more, for example. Moreover, a part in which the amino acid sequence and the amino acid residue are different from those of the polypeptide of (i) above in the polypeptide of (iii) is desirably a part other than the part participating in the sulfatase activity in the polypeptide of (i) above similar to the case of the polypeptide of (ii) above.

The sequence identity of polypeptides is expressed by a numerical value obtained by optimally aligning two polypeptides to be contrasted, dividing the number of the positions at which the amino acids match in both the sequences by a total number of comparative amino acids, and then multiplying the result by 100. Such sequence identity can be determined using known algorithms, such as BLAST and FASTA, for example. A specific operation method for determining the sequence identity is described in "How to Use Database of Genome Network" edited by Toshihisa TAKAGI and Minoru KANEHISA, Second edition (1998), Kyoritsu shuppan (Tokyo, Japan), for example.

In the polypeptide of (iv) above, specific examples of the stringent conditions include a condition of forming a hybrid at 45° C. in a solution containing 6×SSC (supposing that a solution containing 1.5 M NaCl and 0.15 M trisodium citrate is 10×SSC) and 50% formamide, and then washing the same at 50° C. with 2×SSC (Molecular Biology, John Wiley & Sons, N.Y. (1989), 6.3.1-6.3.6).

The polypeptides of (iii) and (iv) above can be obtained by searching and obtaining a gene coding the polypeptides from the genome base sequences of living things, such as microorganisms and mollusks, using known programs and genetic engineering techniques, and then introducing mutation into the gene as necessary to obtain a gene product. The polypeptide of (iii) above can also be obtained by introducing mutation, such as substitution, deletion, addition, and insertion, into the amino acid sequence represented by SEQ ID NO: 1 in the same manner as in the polypeptide of (ii) above.

As the sulfatase to be used in the present invention, it is preferable to produce the sulfatase as recombinant protein by introducing a gene coding the sulfatase into a suitable host cell to obtain a transformant, and then culturing the same based on a known genetic engineering technique but the sulfatase may be obtained from a non-recombinant microorganism culture which produces sulfatase or may be obtained by extraction treatment from non-recombinant microorganisms and mollusks which produce sulfatase.

A method for obtaining sulfatase as recombinant protein is described in J. Biol. Chem. 1998, 273, 25560-25564 and sulfatase can be obtained as recombinant protein according to a technique described in the literature. When sulfatase is obtained as recombinant protein, a sequence for protein purification, such as a His tag, may be added to the C-terminal of the amino acid sequence as necessary in sulfatase insofar as the activity to catalyze hydrolysis of indoxyl sulfuric acid is not blocked and, in addition thereto, a sequence (for example, poly A addition signal and the like) derived from living things utilized as transformants, such as *coliform bacillus*, may be contained.

In the measurement method of the present invention, sulfatase may be used alone or in combination of two or more kinds thereof.

Tetrazolium Salt

The tetrazolium salt to be used in the present invention is a salt of a compound having a tetrazole ring and is not particularly limited insofar as it is reduced to be able to generate a formazan dye. Examples of the tetrazolium salt include, for example, iodotetrazolium (INT), tetrazolium violet (TV), 3-(4,5-dimethyl-2-thiazolyl)-2,5-diphenyl-2H-tetrazolium (MTT), 2-(4-iodine phenyl)-3-(4-nitrophenyl)-5-(2,4-disulfophenyl)-2H-tetrazolium-sodium salt (WST-1), 2-(4-iodine phenyl)-3-(2,4-dinitrophenyl)-5-(2,4-disulfophenyl)-2H-tetrazolium-sodium salt (WST-3), 2-(2-methoxy-4-nitrophenyl)-3-(4-nitrophenyl)-5-(2,4-disulfophenyl)-2H-tetrazolium-sodium salt (WST-8), and nitrotetrazolium blue (NTB), and the like.

As the tetrazolium salt to be used in the present invention, a tetrazolium salt which generates a water-soluble formazan dye when reduced is preferably mentioned and WST-1, WST-3, and WST-8 are more preferably mentioned. In particular, WST-8 has high solubility in water, high sensitivity, and excellent storageability in an aqueous solution state and thus is particularly suitably used in the present invention.

In the measurement method of the present invention, the tetrazolium salts may be used alone or in combination of two or more kinds thereof.

Albumin

In the measurement method of the present invention, albumin may be allowed to coexist when causing sulfatase and tetrazolium salt to act on a sample. Thus, by allowing albumin to coexist, the dilution linearity of a sample can be increased and the measurement accuracy can be further increased.

The albumin to be used in the present invention is not particularly limited and human serum albumin, bovine serum albumin, ovalbumin, and the like are mentioned, for example. The albumin mentioned above may be used alone or in combination of two or more kinds thereof. The albumin mentioned above may be purified from animals or egg white or may be produced as recombinant albumin by a genetic engineering technique.

Among the albumin mentioned above, a human serum albumin is preferably mentioned. In particular, gene-recombinant human serum albumin is free from mixing of human-derived virus and the like and thus is particularly suitably used in the present invention.

Anionic Surfactant and/or Thiol Compound

In the measurement method of the present invention, when causing sulfatase and tetrazolium salt to act on a sample, an anionic surfactant and/or a thiol compound may be allowed to coexist. Thus, by allowing an anionic surfactant and/or a thiol compound to coexist, the dilution linearity of the sample can be increased and also the measurement sensitivity can also be increased, so that the measurement accuracy can be further increased.

The anionic surfactant to be used in the present invention is not particularly limited and may be any one of a carboxylic type, a sulfate ester type, and a sulfonic acid type. The number of carbons of the anionic surfactant to be used in the present invention is not particularly limited and is, for example, 6 to 30, preferably 6 to 20, and more preferably 6 to 15.

Specific examples of the anionic surfactant to be used in the present invention include carboxylic acid type anionic surfactants, such as sodium octanoate, N-lauroylsarcosine sodium salt, cholic acid sodium salt, and sodium deoxycholate; sulfate type anionic surfactants, such as dodecyl sodium sulfate and dodecyl lithium sulfate; sulfonic acid type anionic surfactants, such as sodium dodecylbenzenesulfonate; and the like. These anionic surfactants may be used alone or in combination of two or more kinds thereof.

Among the anionic surfactants, from the viewpoint of more effectively increasing the dilution linearity and the measurement sensitivity of a sample, carboxylic acid type anionic surfactants are preferably mentioned and sodium octanoate and N-lauroylsarcosine sodium salt are more preferably mentioned.

The thiol compound to be used in the present invention is a compound having hydrogenated sulfur at the terminal and having a structure represented by R-SH (R is an organic group). The thiol compound to be used in the present invention is not particularly limited and cysteine; cysteine derivatives, such as homocysteine and N-acetylcysteine; hydroxyl group containing thiol compounds, such as thioglycerol, 2-mercaptoethanol, and dithiothreitol; and the like are mentioned. These thiol compounds may be used alone or in combination of two or more kinds thereof.

Among the thiol compounds, from the viewpoint of more effectively increasing the dilution linearity and the measurement sensitivity of a sample, cysteine and cysteine derivatives are preferably mentioned and N-acetyl cysteine is more preferably mentioned.

In the measurement method of the present invention, when the anionic surfactants and/or the thiol compounds mentioned above are used, only either one of the anionic surfactants or the thiol compounds may be used but it is preferable to use both the anionic surfactants and the thiol compounds from the viewpoint of more effectively increasing the dilution linearity and measurement sensitivity of a sample.

Reaction Conditions

In the measurement method of the present invention, in order to cause sulfatase and tetrazolium salt to act on a sample, a reaction liquid containing the sample, sulfatase, tetrazolium salt and, as necessary, albumin, an anionic surfactant and/or a thiol compound may be prepared, and then may be incubated under temperature conditions which allow the progress of a reaction shown in FIG. 1.

The sample concentration in the reaction liquid is set as appropriate according to the type of the sample to be used, the amount of indoxyl sulfuric acid contained in the sample, and the like. In the measurement method of the present invention, measurement with high accuracy is achieved when the concentration of the indoxyl sulfuric in the reaction liquid acid is about 0.01 to 5 µg/ml and preferably about 0.03 to 2 µg/ml. Therefore, the sample concentration in the reaction liquid may be set as appropriate considering the concentration range in which the measurement can be performed, the sample type, and the like.

The concentration of the sulfatase in the reaction liquid is set as appropriate according to the reaction time, the sample type, and the like and is, for example, 0.1 to 20 U/ml and preferably 0.2 to 10 U/ml. Herein, sulfatase 1 U refers to an amount with which 1 µmol p-nitrophenyl sulfuric acid is hydrolyzed for 1 minute.

The concentration of the tetrazolium salt in the reaction liquid is set as appropriate according to the reaction time, the sample type, and the like and is, for example, 0.01 to 50 mmol/l and preferably 0.05 to 10 mmol/l.

When adding albumin into the reaction liquid, the concentration of the albumin in the reaction liquid is set as appropriate according to the reaction time, the sample type, and the like and is, for example, 0.01 to 5% by weight and preferably 0.04 to 1% by weight.

When adding the anionic surfactant into the reaction liquid, the concentration of the anionic surfactant in the reaction liquid is set as appropriate according to the reaction time, the sample type, and the like and, for example, 0.1 to 50 mmol/l and preferably 0.2 to 10 mmol/l.

When adding the thiol compound into the reaction liquid, the concentration of the thiol compound in the reaction liquid is set as appropriate according to the reaction time, the sample type, and the like and is, for example, 0.01 to 5 mmol/l and preferably 0.02 to 1 mmol/l.

The pH of the reaction liquid may be set in the range where a reaction by sulfatase and tetrazolium salt to be used is not blocked and is, for example, 5 to 12 and preferably 7 to 9.

In order to promote the reduction of the tetrazolium salt, an electron carrier may be added to the reaction liquid as necessary. Specific examples of the electron carrier include phenazine methosulfate (PMS), 1-methoxyphenanzinium methyl sulfate (1-mPMS), 9-dimethylamino benzo-α-phenanzoxonium chloride (Meldola's blue), and the like. The electron carriers may be used alone or in combination of two or more kinds thereof.

In order to eliminate the influence of the coexistence substances in the sample, ascorbate oxidase (ASOD), other surfactants, chelating agents (for example, ethylenediaminetetraacetic acid (EDTA) and the like), and the like may be added to the reaction liquid as necessary. Other additives, such as a pH adjuster, a stabilizer, and an antiseptic (for example, sodium azide and the like) may be added to the reaction liquid in the range where the effects of the present invention are not impaired.

In the measurement method of the present invention, the order of adding the sample, the sulfatase, and the tetrazolium salt when preparing the reaction liquid is not particularly limited and any order described below may be acceptable:

(i) The sample, the sulfatase, and the tetrazolium salt are simultaneously added;

(ii) The sulfatase and the tetrazolium salt are simultaneously added into a solution containing the sample, (iii) The tetrazolium salt is added into a solution containing the sample, and then the sulfatase is added thereinto;

(iv) The sulfatase is added into a solution containing the sample, and then the tetrazolium salt is added thereinto; and the like. From the viewpoint of inhibiting a side reaction and measuring indoxyl sulfuric acid with high accuracy, a method including adding the tetrazolium salt into the solution containing the sample, heating the mixture at the same heating temperature as the temperature of generating a formazan dye for about 1 to 10 minutes to set the temperature of the solution to a fixed temperature, and then adding the sulfatase to prepare the reaction liquid is preferably mentioned. In the measurement method of the present invention, when adding albumin or the anionic surfactant and/or the thiol compound into the reaction liquid, the addition order thereof is not particularly limited insofar as the sulfatase and the tetrazolium salt can act on the sample in the coexistence of these additives.

The temperature conditions when incubating the reaction liquid is set as appropriate in the range where the temperature is the action temperature of the sulfatase and the tetrazolium salt can be reduced and is, for example, 10 to 50° C. and preferably 20 to 40° C.

The incubation time of the reaction liquid is also set as appropriate according to the type of the sample to be used, the concentration of the sulfatase and the tetrazolium salt, and the like. The incubation time is, for example, 1 to 120 minutes, preferably 1 to 30 minutes, and more preferably 1 to 10 minutes, for example. Herein, the "incubation time" refers to time measured setting the time where the sample, the sulfatase, and the tetrazolium salt coexist as the starting point.

Measurement of Formazan Dye

The formazan dye is generated by incubating the reaction liquid containing the sample, the sulfatase, and the tetrazolium salt as described above. The concentration of the generated formazan dye reflects the indoxyl sulfuric acid concentration in the sample. Therefore, the indoxyl sulfuric acid concentration in the sample can be measured by determining the concentration of the generated formazan dye.

A method for measuring the concentration of the formazan dye is not particularly limited and known former methods may be employed and a method for measuring the absorbance of the formazan dye by absorption spectrophotometry is preferably mentioned. The wavelength when measuring the absorbance of the formazan dye is set as appropriate according to the type of the tetrazolium salt to be used and the generated formazan dye and is not limited insofar as the wavelength is a wavelength at which the formazan dye can be specifically absorbed. The wavelength is usually set within the range of 340 to 700 nm. More specifically, the absorbance at 450 nm may be measured when using WST-8 as the tetrazolium salt.

In the measurement method of the present invention, when the tetrazolium salt, such as MTT and NTB, is used, a formazan dye which is insoluble or is difficult to solve in water is generated. In the system in which such a formazan dye which is insoluble or is difficult to solve in water is generated, the formazan dye may be dissolved with organic solvents, such as isopropanol, and then the absorbance may be measured.

When measuring the concentration of the formazan dye, a value obtained by measuring the absorbance (absorbance A) of the formazan dye before starting the incubation and the absorbance (absorbance B) of the formazan dye when the incubation is completed, and then subtracting the absorbance A from the absorbance B is the absorbance corresponding to the concentration of the generated formazan dye. For example, in the case where the tetrazolium salt is added into the solution containing the sample, and then the sulfatase is added, the tetrazolium salt is added into the solution containing the sample, the absorbance (absorbance A) of the formazan dye is measured, the sulfatase is added and incubated, the absorbance (absorbance B) of the formazan dye is measured, and then a value obtained by subtracting the absorbance A from the absorbance B is calculated as the absorbance corresponding to the concentration of the generated formazan dye.

When the concentration of the formazan dye to be generated is measured using indoxyl sulfuric acid having a known concentration, and then the calibration curve is created beforehand, the indoxyl sulfuric acid concentration in the sample can also be quantitatively measured.

2. Kit for Measuring Indoxyl Sulfuric Acid

The present invention further provides a kit for measuring indoxyl sulfuric acid containing sulfatase and tetrazolium salt. The kit of the present invention is used in order to carry out the method for measuring indoxyl sulfuric acid described above.

In the kit of the present invention, the sulfatase and the tetrazolium salt may be a single component configuration or a two-component configuration. More specifically, the kit of the present invention may contain a reagent (hereinafter also referred to as a "single component configuration reagent") containing sulfatase and tetrazolium salt. However, an aspect is preferably mentioned in which a first reagent (hereinafter also referred to as a "first reagent of a two-component configuration") containing tetrazolium salt and a second reagent (hereinafter also referred to as a "second reagent of a two-component configuration") containing sulfatase are individually contained.

The one-component configuration reagent, the first reagent of the two-component configuration, and the second reagent of the two-component configuration may be liquid or may be a solid, such as a freeze-dried state.

The one-component configuration reagent, the first reagent of the two-component configuration, and the second reagent of the two-component configuration may contain, as necessary, additives to be added to the reaction liquid, such as a buffer, an electron carrier, ascorbate oxidase (ASOD), a surfactant, a chelating agent (for example, ethylenediaminetetraacetic acid (EDTA) and the like), a pH adjuster, a stabilizer, and an antiseptic (for example, sodium azide and the like). The kit of the present invention may further contain a third reagent containing various additives to be used for pretreatment, promotion of a reaction, and the like of a sample in addition to the one-component configuration reagent, the first reagent of the two-component configuration, and the second reagent of the two-component configuration.

The kit of the present invention may further contain albumin. In the case where the kit of the present invention has the two-component configuration containing the first reagent of the two-component configuration and the second reagent of the two-component configuration and albumin contain is blended, the albumin may be contained in either the first reagent of the two-component configuration or the second reagent of the two-component configuration and is preferably contained in the first reagent of the two-component configuration.

The kit of the present invention may further contain an anionic surfactant and/or a thiol compound. In the case where the kit of the present invention has the two-component configuration containing the first reagent of the two-component configuration and the second reagent of the two-component configuration and an anionic surfactant and/or a thiol compound are/is blended, the anionic surfactant and/or the thiol compound each may be contained in either the first reagent of the two-component configuration or the second reagent of the two-component configuration. The anionic surfactant is preferably contained in the first reagent of the two-component configuration.

The kit of the present invention may further contain indoxyl sulfuric acid having a known concentration to be used for the creation of the calibration curve, a diluted solution to be used for dilution of a sample and the like, and the like. The kit of the present invention may contain a measurement manual showing the measurement conditions of the indoxyl sulfuric acid.

Since it is known that the indoxyl sulfuric acid concentration in a living body has a correlation with renal dysfunction as described above, the kit of the present invention can be used as a kit for diagnosis of renal function and is particularly suitable as a kit for diagnosis of diseases accompanied by lowering of renal function. Specific examples of the diseases accompanied by lowering of renal function include renal failure (acute renal failure and chronic renal failure), uremia, and the like. Among the above, with respect to the renal failure, particularly the chronic renal failure, the indoxyl sulfuric acid concentration in blood of patients is high and high correlation is recognized between the indoxyl sulfuric acid concentration in blood and the level of the disease symptoms, the kit of the present invention is very useful for diagnosis of the renal failure, particularly the chronic renal failure.

3. Method for Examining Renal Function

The present invention also provides a method for examining renal function utilizing the method for measuring indoxyl sulfuric acid described above.

The indoxyl sulfuric acid concentration in samples derived from a living body, such as blood, serum, plasma, and urine, reflects renal function and may serve as an index for examining diseases accompanied by lowering of renal function as described above. Therefore, the method for measuring indoxyl sulfuric acid can be applied to the examination of renal function.

The method for examining renal function of the present invention includes a process of causing sulfatase and tetrazolium salt to act on a sample extracted from a living body, and then measuring a generated formazan dye.

The sample to be used in the method for examining renal function of the present invention may be one extracted from a human being who needs to be subjected to the examination of renal function and, for example, blood, serum, plasma, urine, and the like may be acceptable and blood, serum, and plasma are preferably mentioned and serum and plasma are more preferably mentioned.

In the method for examining renal function of the present invention, renal function can be examined by determining the concentration of indoxyl sulfuric acid contained in the sample from a generated formazan dye, and then comparing the determined concentration with the indoxyl sulfuric acid concentration in a sample extracted from a healthy person. Specifically, it is judged that renal function is lowered when the indoxyl sulfuric acid concentration in the sample is higher than that of a healthy person and it is judged that renal function is normal when the indoxyl sulfuric acid concentration in the sample is almost equal to that of a healthy person.

The method for examining renal function of the present invention is particularly useful as a method for examining the diseases accompanied by lowering of renal function. Specific examples of the diseases accompanied by lowering of renal function are as mentioned above.

The results obtained by the method for examining renal function of the present invention can serve as indices for judgment of the presence or absence of the diseases accompanied by lowering of renal function, judgment of therapeutic effects of the diseases, prognostic prediction of the patients with the diseases, selection of prescription foods of dietary therapy in the patients with the diseases, and the like.

EXAMPLES

Hereinafter, the present invention is described in more detail with reference to Test Examples and the like but the present invention is not particularly limited thereto.

Production Example 1: Preparation of Sulfatase Derived from *Pseudomonas aeruginosa*

(1) Cloning of Sulfatase Gene

A sulfatase gene was amplified by a polymerase chain reaction (PCR) using a genome DNA (NBRC 106052G) derived from *Pseudomonas aeruginosa* as a template. A PCR primer was designed based on the sulfatase gene sequence information of a database. The sequence of the primer is shown in each of SEQ ID NO: 1 (Forward Primer) and SEQ ID NO: 2 (Reverse Primer) of the sequence listing. A recognition sequence of a restriction enzyme EcoRI was introduced into the primer of SEQ ID NO: 1 and a recognition sequence of SalI was introduced into the primer of SEQ ID NO: 2.

The PCR reaction was performed using PrimeSTAR DNA polymerase (manufactured by TAKARA SHUZO CO., LTD.) with iCycler (manufactured by BioRAD) by performing 30 cycles of thermal denaturation at 98° C. for 10 seconds, annealing at 53° C. for 15 seconds, and extension reaction at 72° C. for 50 seconds. As a result, fragments having a target size of about 1620 bp were amplified. The amplified fragments were sequenced, and then it was confirmed that the base sequence of the PCR product is the same as the *Pseudomonas aeruginosa* sulfatase gene sequence of the database.

(2) Production of Recombinant Vector and Preparation of Transformant

A recombinant vector containing a gene coding a sulfatase gene was produced. The DNA fragment of the PCR product obtained (1) above was cut by a restriction enzyme EcoRI (manufactured by TAKARA SHUZO CO., LTD.) and a restriction enzyme SalI (manufactured by TAKARA SHUZO CO., LTD.). On the other hand, plasmid vector pTrc99a was cut by the same restriction enzymes, and then isolated by agarose gel electrophoresis. Then, DNA fragments having a larger molecular weight were collected using GenElute Gel Extraction Kit (manufactured by SIGMA-ALDRICH). Subsequently, the DNA fragments were allowed to react at 16° C. for 15 minutes with Ligationhigh kit (manufactured by Toyobo) to be combined to obtain a recombinant vector containing a sulfatase gene derived from *Pseudomonas aeruginosa*.

Then, the recombinant vector was introduced into a competent cell (manufactured by Toyobo) of *Escherichia coli* DH5a, applied to an LB agar medium containing 100 µg/ml of ampicillin, and then cultured at 37° C. all night to obtain a transformant. A plasmid was extracted from the transformant, and then purified to obtain a recombinant vector.

The obtained recombinant vector has an initiation codon before an initiation codon of the sulfatase gene, and therefore an excessive amino acid sequence is added to the N-terminal of the sulfatase gene. Then, an inverse PCR was performed using the obtained recombinant vector as a template to thereby delete the excessive sequence. The base sequence of the primer used for the inverse PCR is represented by SEQ ID NO: 3 (Forward Primer) and SEQ ID NO: 4 (Reverse Primer) of the sequence listing. The PCR reaction was performed by performing 12 cycles of thermal denaturation at 98° C. for 10 seconds, annealing at 53° C. for 15 seconds, and extension reaction at 72° C. for 4 minutes. The template DNA was cut by performing restriction enzyme treatment of the obtained PCR product with DpnI, and then the 5'-terminal of the amplified DNA fragments was phosphorylated with T4 polynucleotide kinase. Subsequently, the DNA fragments were allowed to react at 16° C. for 15 minutes with Ligationhigh kit (manufactured by Toyobo) to be combined, introduced into a competent cell (manufactured by Toyobo) of *Escherichia coli* DH5a, and then a transformant was obtained by the same method as described above. A plasmid was extracted from the transformant, and then purified to obtain a recombinant vector. The obtained recombinant vector was named as pTrc-SFT. Furthermore, the pTrc-SFT was introduced into a competent cell of *Escherichia coli* BL21 to obtain a transformant.

(3) Production of Sulfatase Enzyme from Transformant

The obtained transformant BL21 (pTrc-SFT) was inoculated in a 30 ml LB liquid medium (1.0% polypeptone, 0.5% yeast extract, 0.5% NaCl, and 100 µg/ml ampicillin), and then cultured at 37° C. for 16 hours to obtain a seed culture liquid. The whole quantity of the culture solution was inoculated in 1.5 L of 4×YT (3 L jar fermenter; 3.2% polypeptone, 2.0% yeast extract, 0.5% NaCl, and 1.0% glycerol, pH 7.5), and then stirred and cultured under aeration at 30° C. for 68 hours. The sulfatase activity of the culture solution when completing the culture was about 6.0 U/ml. The sulfatase activity is indicated setting the hydrolyzed amount of 1 µmol p-nitrophenyl sulfuric acid for 1 minute in a Tris hydrochloric acid buffer solution (pH 8.0) at 37° C. as 1 U.

A fungus body was collected by centrifugal separation, and then suspended in 20 mM Tris hydrochloric acid buffer solution (pH 8.0). Then, the fungus body was crushed by an ultrasonic crusher to obtain a coarse enzyme liquid. The coarse enzyme liquid was introduced into a DEAE-Sepharose column equilibrated with 20 mM of Tris hydrochloric acid buffer solution (pH 8.0), and then eluted by a potassium chloride concentration gradient of 0 to 80% to collect a sulfatase enzyme active fraction. The sulfatase isolated and purified by this method was used in Test Examples 1 and 2 below as a purified enzyme preparation.

Example 1: Preparation of Kit for Measuring Indoxyl Sulfuric Acid-1

A first reagent and a second reagent of the following compositions were prepared as a kit for measuring indoxyl sulfuric acid.

First Reagent
  Tris hydrochloric acid buffer solution (pH 8.0): 100 mM
  WST-8: 0.5 mM
  EDTA: 1 mM
  Sodium azide: 0.1%
Second Reagent
  Tris hydrochloric acid buffer solution (pH 8.0): 100 mM
  Sulfatase derived from *Pseudomonas aeruginosa* obtained in Production Example 1: 10 KU/L
  EDTA: 1 mM
  Sodium azide: 0.1%

Example 2: Measurement Using Physiological Saline Containing Indoxyl Sulfuric Acid Having Known Concentration as Sample The indoxyl sulfuric acid concentration in a sample was measured using the kit for measuring indoxyl sulfuric acid of Example 1 with a H7180 type automatic analyzer (Hitachi High-Technologies Corp.). As the sample, physiological saline containing 4% HSA (human serum albumin) in which the indoxyl sulfuric acid concentration was adjusted to be 0.1 to 5.0 mg/dl was used. Specific measurement conditions are as described below.

Figure 2:
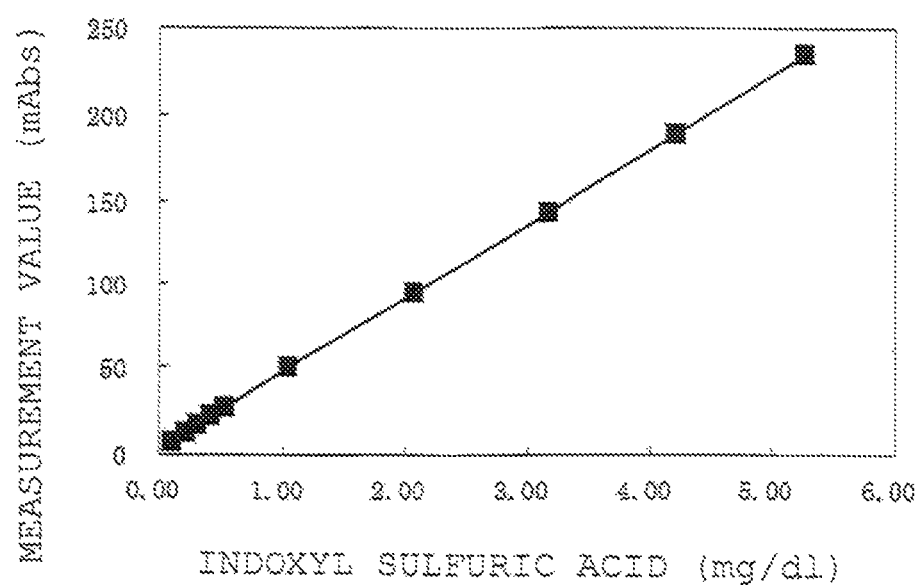
FIG. 2 is a view showing the relationship between the measured absorbance (vertical axis) and the known indoxyl sulfuric acid concentration (horizontal axis) in a sample in Example 1.

160 µl of the first reagent was mixed with 8 µl of the sample, and then warmed at 37° C. for 5 minutes. Then, the absorbance (absorbance A) at 450 nm was measured. Next, 40 µl of the second reagent was added, and then warmed at 37° C. for 5 minutes. Then, the absorbance (absorbance B) at 450 nm was measured. A value obtained by subtracting the absorbance A from the absorbance B was defined as the measurement value. The obtained results are shown in FIG. 2. In FIG. 2, the actual measurement values (absorbance) were plotted on the vertical axis and the known indoxyl sulfuric acid concentrations in the sample were plotted on the horizontal axis.

As is clear from FIG. 2, good linearity was obtained between the known indoxyl sulfuric acid concentration in the sample and the actual measurement values (absorbance) obtained after causing the first known reagent and the second reagent to act. More specifically, the results showed that the concentration of a generated formazan dye correctly reflects the indoxyl sulfuric acid concentration in the sample.

Example 3: Measurement Using Serum Sample Containing Indoxyl Sulfuric Acid Having Known Concentration The absorbance of the concentration of a generated formazan pigment was measured by the same method as that of Example 2, except using a serum sample obtained by adding indoxyl sulfuric acid having a known concentration to a commercially available control serum QAP trol 1× or QAP trol 2× (Sysmex Corp.).

The absorbance of the concentration of a generated formazan pigment by the same method as the method above was measured using physiological saline containing 4% HSA in which the indoxyl sulfuric acid concentration was adjusted to be 1 mg/dl as a sample, and then the absorbance of a formazan dye generated when the indoxyl sulfuric acid concentration was 1 mg/dl was determined. The concentration of indoxyl sulfuric acid contained in the serum sample was calculated based on the relationship of the indoxyl sulfuric acid concentration and the absorbance of the formazan dye.

The obtained results are shown in Table 1. In Table 1, an additional recovery refers to a ratio (%) of the indoxyl sulfuric acid concentration (measurement concentration) in the serum sample obtained by the measurement to the concentration (additive concentration) of the indoxyl sulfuric acid added to the serum sample. As a result, the additional recovery of the indoxyl sulfuric acid was almost 100% and the concentration of the indoxyl sulfuric acid added to the serum sample and the actually measured indoxyl sulfuric acid concentration had almost the same value. The results above proved that, when the first reagent and the second reagent of Example 1 were used, the indoxyl sulfuric acid concentration in serum can be correctly measured.

TABLE 1

| Control serum | Concentration of indoxyl sulfuric acid added to serum sample (Additive concentration) | Concentration of indoxyl sulfuric acid in serum sample obtained by measurement (Measurement concentration) | Additional recovery |
|---|---|---|---|
| QAP trol 1× | 0.102 mg/dl | 0.108 mg/dl | 106% |
|  | 0.963 mg/dl | 1.033 mg/dl | 107% |
| QAP trol 2× | 0.096 mg/dl | 0.103 mg/dl | 108% |
|  | 1.006 mg/dl | 1.063 mg/dl | 105% |

Example 4: Preparation of Kit for Measuring Indoxyl Sulfuric Acid-2

A first reagent and a second reagent of the following compositions were prepared as a kit for measuring indoxyl sulfuric acid.
First Reagent
  Tris hydrochloric acid buffer solution (pH 8.0): 100 mM
  WST-8: 0.1 mM
Second Reagent
  Tris hydrochloric acid buffer solution (pH 8.0): 100 mM
  Sulfatase derived from *Pseudomonas aeruginosa* obtained in Production Example 1: 10 KU/L Example 5: Preparation of Kit for Measuring Indoxyl Sulfuric Acid-3

A first reagent and a second reagent of the following compositions were prepared as a kit for measuring indoxyl sulfuric acid.
First Reagent
  Tris hydrochloric acid buffer solution (pH 8.0): 100 mM
  WST-8: 0.1 mM
Second Reagent
  Tris hydrochloric acid buffer solution (pH 8.0): 100 mM
  Sulfatase derived from commercially available *Helix pomatia* (manufactured by SIGMA-ALDRICH, Product Number S9626): 10 KU/L Example 6: Measurement Using Physiological Saline Containing Indoxyl Sulfuric Acid Having Known Concentration as Sample The indoxyl sulfuric acid concentration in a sample was measured using the kits for measuring indoxyl sulfuric acid of Examples 4 and 5 with a spectrum photometer UV-265 (Shimadzu Corp.). As the sample, physiological saline in which the indoxyl sulfuric acid concentration was adjusted to be 10 mg/dl was used. Specific measurement conditions are as described below.

800 µl of the first reagent was mixed with 40 µl of the sample, and then warmed at 37° C. for 5 minutes. Then, the absorbance (absorbance A) at 450 nm was measured. Next, 200 µl of the second reagent was added, and then warmed at 37° C. Then, the absorbance (absorbance B) at 450 nm 5 minutes later after the addition of the second reagent and the absorbance (absorbance B) at 450 nm 90 minutes after the addition of the second reagent were measured. A value obtained by subtracting the absorbance A from the absorbance B was defined as the measurement value.

The obtained results are shown in Table 2. In the sulfatase derived from *Pseudomonas aeruginosa*, when 10 mg/dl indoxyl sulfuric acid was used as the sample, an increase in the absorbance at 450 nm due to the formazan dye generation was observed and the sulfatase activity to the indoxyl sulfuric acid was confirmed. On the other hand, also in the sulfatase derived from *Helix pomatia*, when 10 mg/dl indoxyl sulfuric acid was used as the a sample, an increase in the absorbance at 450 nm due to the formazan dye generation was confirmed but the increase was lower than the increase in the sulfatase derived from *Pseudomonas aeruginosa*.

TABLE 2

| | Changes in absorbance at 450 nm | | | |
|---|---|---|---|---|
| | Physiological saline | | Physiological saline containing 10 mg/dl indoxyl sulfuric acid | |
| | 5 minutes later | 90 minutes later | 5 minutes later | 90 minutes later |
| Example 4 | 0.009 | 0.013 | 0.352 | 0.352 |
| Example 5 | 0.019 | 0.023 | 0.022 | 0.041 |

Example 7: Preparation of Kit for Measuring Indoxyl Sulfuric Acid-4

A first reagent and a second reagent of the following compositions were prepared as a kit for measuring indoxyl sulfuric acid.
First Reagent
  PIPES buffer solution (pH 7.0): 50 mM
  1-mPMS (manufactured by Dojin Chemical Laboratory, Product Number M003): 0.05 mM
  Gene recombinant human serum albumin (HSA) (manufactured by Wako Pure Chemical Industries, Ltd., Product Number 014-21543): 0.5% by weight Second Reagent
  Tris hydrochloric acid buffer solution (pH 8.2): 200 mM
  WST-8: 1 mM
  Sulfatase derived from *Pseudomonas aeruginosa* obtained in Production Example 1: 10 KU/L Example 8: Preparation of Kit for Measuring Indoxyl Sulfuric Acid-5

A first reagent and a second reagent of the following compositions were prepared as a kit for measuring indoxyl sulfuric acid.
First Reagent
  HEPES buffer solution (pH 7.8): 100 mM
  WST-8: 0.25 mM
  Sodium octanoate (manufactured by Wako Pure Chemical Industries, Ltd., Product Number 196-08192): 5 mM
Second Reagent
  HEPES buffer solution (pH 7.8): 100 mM
  N-acetyl cysteine (manufactured by Roche, Product Number 068365): 2.5 mM
  Sulfatase derived from *Pseudomonas aeruginosa* obtained in Production Example 1: 15 KU/L Example 9: Measurement of Dilution Linearity Using Serum Sample Containing Indoxyl Sulfuric Acid Having Known Concentration Samples obtained by diluting a serum sample, in which 4 to 6 mg/dl of indoxyl sulfuric acid was added to a commercially available control serum, by 4 times, 16 times, and 64 times with physiological saline were measured for the absorbance of the concentration of a generated formazan dye by the same method as the method of Example 2 using the kits for measuring indoxyl sulfuric acid of Examples 1, 7, and 8.

Moreover, the absorbance of the concentration of a generated formazan dye was measured by the same method as the method above using physiological saline containing 4% by weight of HSA in which the indoxyl sulfuric acid concentration was adjusted to be 1 mg/dl as a sample, and then the absorbance of a formazan dye generated when the indoxyl sulfuric acid concentration was 1 mg/dl was determined. Based on the relationship of the indoxyl sulfuric acid concentration and the absorbance of the formazan dye, the concentration of the indoxyl sulfuric acid contained in the sample was calculated.

Figure 3:
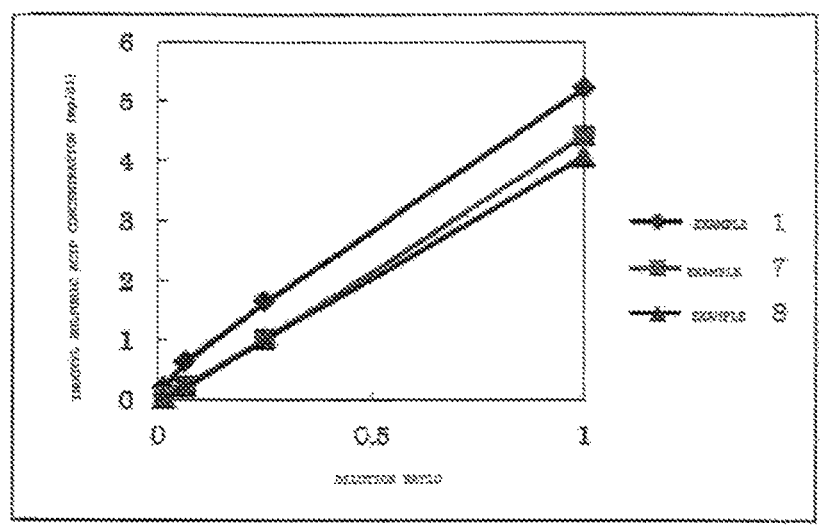
FIG. 3 is a view showing the relationship between the measured absorbance (vertical axis) and the dilution magnification (horizontal axis) of a serum sample to which indoxyl sulfuric acid is added in Example 9.

The obtained results are shown in FIG. 3. In FIG. 3, the measurement values were plotted on the vertical axis and the dilution magnifications were plotted on the horizontal axis. As a result, it was proved that the kits for measuring indoxyl sulfuric acid of Examples 7 and 8 had more excellent dilution linearity of the serum sample than that of the kit for measuring indoxyl sulfuric acid of Example 1. More specifically, the test results clarified that when sulfatase and tetrazolium salt were caused to act in the presence of albumin or in the presence of an anionic surfactant and a thiol compound, the dilution linearity of the samples containing indoxyl sulfuric acid is improved.

The absorbance of the formazan dye generated when the indoxyl sulfuric acid concentration is 1 mg/dl is shown in Table 3. As a result, it was proved that the kit for measuring indoxyl sulfuric acid of Example 8 had more excellent measurement sensitivity than that of the kits for measuring indoxyl sulfuric acid of Examples 1 and 7. More specifically, the test results clarified that, when sulfatase and tetrazolium salt were caused to act in the presence of an anionic surfactant and a thiol compound, an improvement of the measurement sensitivity of indoxyl sulfuric acid is also recognized.

TABLE 3

|  | Example 1 | Example 2 | Example 3 |
| --- | --- | --- | --- |
| Changes in absorbance of 1 mg/dl indoxyl sulfuric acid (mAbs.) | 50.5 | 43.6 | 76.8 |

Sequence Listing Free Text
  SEQ ID No. 3 shows the base sequence of Forward Primer used for the amplification of a sulfatase gene.
  SEQ ID No. 4 shows the base sequence of Reverse Primer used for the amplification of a sulfatase gene.
  SEQ ID No. 5 shows the base sequence of Forward Primer used for the inverse PCR.
  SEQ ID No. 6 shows the base sequence of Reverse Primer used for the inverse PCR.

The invention claimed is:

1. A method for measuring indoxyl sulfuric acid contained in a sample, comprising:

admixing the sample with a reaction mixture comprising (i) a sulfatase, (ii) a tetrazolium salt, and (iii) at least one selected from the group consisting of an anionic surfactant, a thiol compound, and combinations thereof, wherein the sulfatase reacts with the indoxyl sulfuric acid contained in the sample to generate indoxyl, and the indoxyl reduces the tetrazolium salt to formazan dye; and measuring a concentration of the formazan dye, wherein the concentration of the formazan dye correlates to a concentration of the indoxyl sulfuric acid contained in the sample.

2. The measurement method according to claim 1, wherein the sulfatase is aryl sulfatase.

3. The measurement method according to claim 1, wherein the sulfatase is derived from at least one kind of microorganism selected from the group consisting of *Pseudomonas*, *Mycobacterium*, *Acinetobacter*, *Streptomyces*, and *Aspergillus*.

4. The measurement method according to claim 1, wherein the sulfatase is derived from bacteria belonging to *Pseudomonas*.

5. The measurement method according to claim 1, wherein the sulfatase is derived from *Pseudomonas aeruginosa*.

6. The measurement method according to claim 1, wherein the sulfatase is aryl sulfatase containing polypeptide selected from the group consisting of:

(i) Polypeptide containing an amino acid sequence represented by SEQ ID NO: 1;

(ii) Polypeptide containing an amino acid sequence in which one or more amino acid residues are substituted, deleted, added, or inserted in the amino acid sequence represented by SEQ ID NO: 1 and having an activity to catalyze a hydrolysis reaction of indoxyl sulfuric acid equal to or higher than the activity of the polypeptide (i) above;

(iii) Polypeptide containing an amino acid sequence having 60% or more sequence identity to the amino acid sequence represented by SEQ ID NO: 1 and having an activity to catalyze a hydrolysis reaction of indoxyl sulfuric acid equal to or higher than the activity of the polypeptide (i) above;

(iv) Polypeptide containing an amino acid sequence coded by a base sequence which can be hybridized to a complementary sequence of a base sequence represented by SEQ ID NO: 2 under stringent conditions and having an activity to catalyze a hydrolysis reaction of indoxyl sulfuric acid equal to or higher than the activity of the polypeptide (i) above, and combinations thereof.

7. The measurement method according to claim 1, wherein the reaction mixture further comprises albumin.

8. A method for examining renal function comprising:

admixing a sample extracted from a living body with a reaction mixture comprising (i) a sulfatase, (ii) a tetrazolium salt, and (iii) at least one selected from the group consisting of an anionic surfactant, a thiol compound, and combinations thereof, wherein the sulfatase reacts with the indoxyl sulfuric acid contained in the sample to generate indoxyl, and the indoxyl reduces the tetrazolium salt to formazan dye;

and measuring a concentration of the formazan dye, wherein the concentration of the formazan dye correlates to a concentration of the indoxyl sulfuric acid contained in the sample.

9. The examination method according to claim 8, wherein the sample is at least one of blood, serum, plasma, or urine.

10. The method of claim 8, wherein the reaction mixture consists of a sulfatase, a tetrazolium salt, and optionally one or more of albumin, anionic surfactant, thiol, water, organic solvent, electron carrier, ascorbate oxidase, chelating agent, pH adjuster, stabilizer, buffer, antiseptic, and any combination thereof.

11. A method for measuring indoxyl sulfuric acid contained in a sample, comprising:

admixing the sample with a reaction mixture consisting of a sulfatase, a tetrazolium salt, and optionally one or more of albumin, anionic surfactant, thiol, water, organic solvent, electron carrier, ascorbate oxidase, chelating agent, pH adjuster, stabilizer, buffer, antiseptic, and any combination thereof, wherein the sulfatase reacts with the indoxyl sulfuric acid contained in the sample to generate indoxyl, and the indoxyl reduces the tetrazolium salt to formazan dye; and measuring a concentration of the formazan dye wherein the concentration of the formazan dye correlates to a concentration of the indoxyl sulfuric acid contained in the sample.

12. The measurement method according to claim 11, wherein the sulfatase is aryl sulfatase.

13. The measurement method according to claim 11, wherein the sulfatase is derived from at least one kind of microorganism selected from the group consisting of *Pseudomonas, Mycobacterium, Acinetobacter, Streptomyces*, and *Aspergillus*.

14. The measurement method according to claim 11, wherein the sulfatase is derived from bacteria belonging to *Pseudomonas*.

15. The measurement method according to claim 11, wherein the sulfatase is derived from *Pseudomonas aeruginosa*.

16. The measurement method according to claim 11, wherein the sulfatase is aryl sulfatase containing polypeptide selected from the group consisting of:

(i) Polypeptide containing an amino acid sequence represented by SEQ ID NO: 1;

(ii) Polypeptide containing an amino acid sequence in which one or more amino acid residues are substituted, deleted, added, or inserted in the amino acid sequence represented by SEQ ID NO: 1 and having an activity to catalyze a hydrolysis reaction of indoxyl sulfuric acid equal to or higher than the activity of the polypeptide (i) above;

(iii) Polypeptide containing an amino acid sequence having 60% or more sequence identity to the amino acid sequence represented by SEQ ID NO: 1 and having an activity to catalyze a hydrolysis reaction of indoxyl sulfuric acid equal to or higher than the activity of the polypeptide (i) above; and (iv) Polypeptide containing an amino acid sequence coded by a base sequence which can be hybridized to a complementary sequence of a base sequence represented by SEQ ID NO: 2 under stringent conditions and having an activity to catalyze a hydrolysis reaction of indoxyl sulfuric acid equal to or higher than the activity of the polypeptide (i) above, and combinations thereof.

17. The measurement method according to claim 11, wherein the reaction mixture comprises albumin.

* * * * *